United States Patent [19]

Akers, Jr.

[11] Patent Number: 5,231,035
[45] Date of Patent: Jul. 27, 1993

[54] LATEX AGGLUTINATION ASSAY

[75] Inventor: Raymond F. Akers, Jr., Sewell, N.J.

[73] Assignee: Akers Research Corporation, Thorofare, N.J.

[21] Appl. No.: 640,037

[22] Filed: Jan. 11, 1991

[51] Int. Cl.$^5$ .................. G01N 33/538; G01N 33/545
[52] U.S. Cl. ...................... 436/531; 436/518;
436/523; 436/524; 436/527; 436/528; 436/529;
436/534; 436/536; 436/538; 436/541; 436/805;
436/815; 436/816; 436/817; 436/818
[58] Field of Search ............... 436/518, 523, 524, 527,
436/528, 529, 531, 534, 805, 815-818, 536, 538, 541

[56] References Cited

U.S. PATENT DOCUMENTS

| | | | |
|---|---|---|---|
| 4,043,989 | 8/1977 | Schneider et al. | 260/112 |
| 4,108,974 | 8/1978 | Wegfahrt et al. | 424/1 |
| 4,226,747 | 10/1980 | Roncari | 260/8 |
| 4,234,654 | 1/1981 | Schneider et al. | 424/12 |
| 4,256,834 | 3/1981 | Zuk et al. | 435/7 |
| 4,292,038 | 9/1981 | Kondo et al. | 23/230 |
| 4,366,241 | 12/1982 | Tom et al. | 435/7 |
| 4,419,453 | 12/1983 | Dorman et al. | 436/534 |
| 4,444,880 | 4/1984 | Tom | 435/7 |
| 4,454,233 | 6/1984 | Wang | 436/525 |
| 4,459,361 | 7/1984 | Gefter | 436/523 |
| 4,542,103 | 9/1985 | Adams | 436/534 |
| 4,552,839 | 11/1985 | Gould et al. | 435/7 |
| 4,703,018 | 10/1987 | Craig et al. | 436/518 |
| 4,727,022 | 2/1988 | Skold et al. | 435/7 |
| 4,738,932 | 4/1988 | Yabusaki | 436/511 |
| 4,808,518 | 2/1989 | Dorsett et al. | 435/5 |
| 4,812,414 | 3/1989 | Warren, III et al. | 436/533 |
| 4,847,199 | 7/1989 | Snyder et al. | 435/36 |
| 4,952,520 | 8/1990 | Okusa et al. | 436/523 X |
| 5,126,242 | 6/1992 | Hachmann et al. | 436/534 X |

OTHER PUBLICATIONS

Masson, et al., *Methods in Enzymology*, 1981, 74, 106-139.

*Primary Examiner*—David Saunders
*Assistant Examiner*—Christopher L. Chin
*Attorney, Agent, or Firm*—Woodcock, Washburn, Kurtz, Mackiewicz & Norris

[57] ABSTRACT

Methods for determining the presence of a first ligand, preferably a hapten, in a sample suspected to contain the first ligand are provided, along with reagent systems and apparatus suitable for performing the methods. The methods depend upon a color visualization indicating the presence or absence of the first ligand in the sample. Preferred methods comprise contacting the sample with a reagent system which comprises: (1) colored particles which bear on their surface a second ligand which may be the same as or different than the first ligand; and (2) an amount of a receptor which is specific for the first ligand and the second ligand, wherein the amount is sufficient to stabilize the particles. The methods further comprise passing the contacted sample and reagent system through a filter, and then analyzing the color of the filtrate. The presence of ligand in the sample is established where the color of the filtrate is substantially different from the color of the ligand-bearing particles.

26 Claims, 2 Drawing Sheets

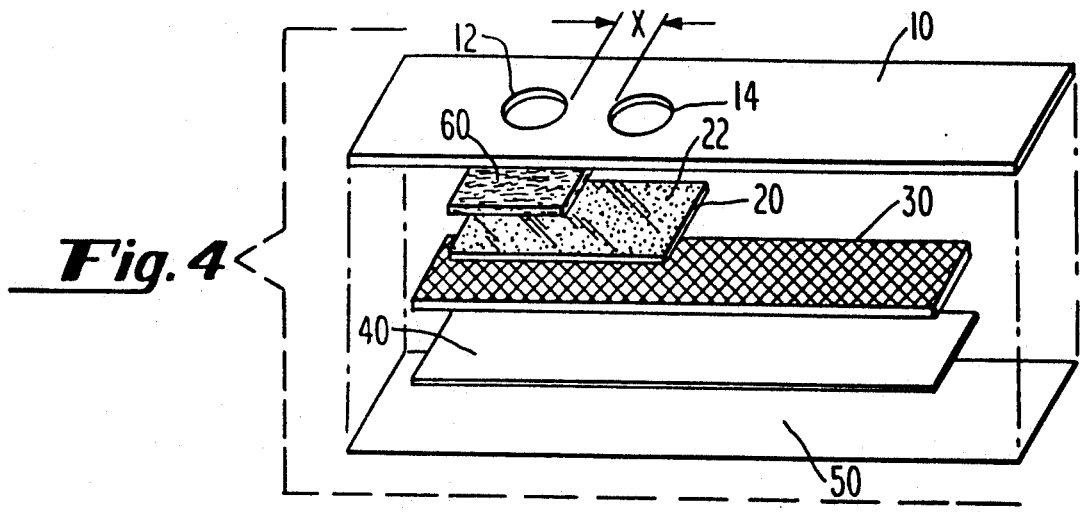
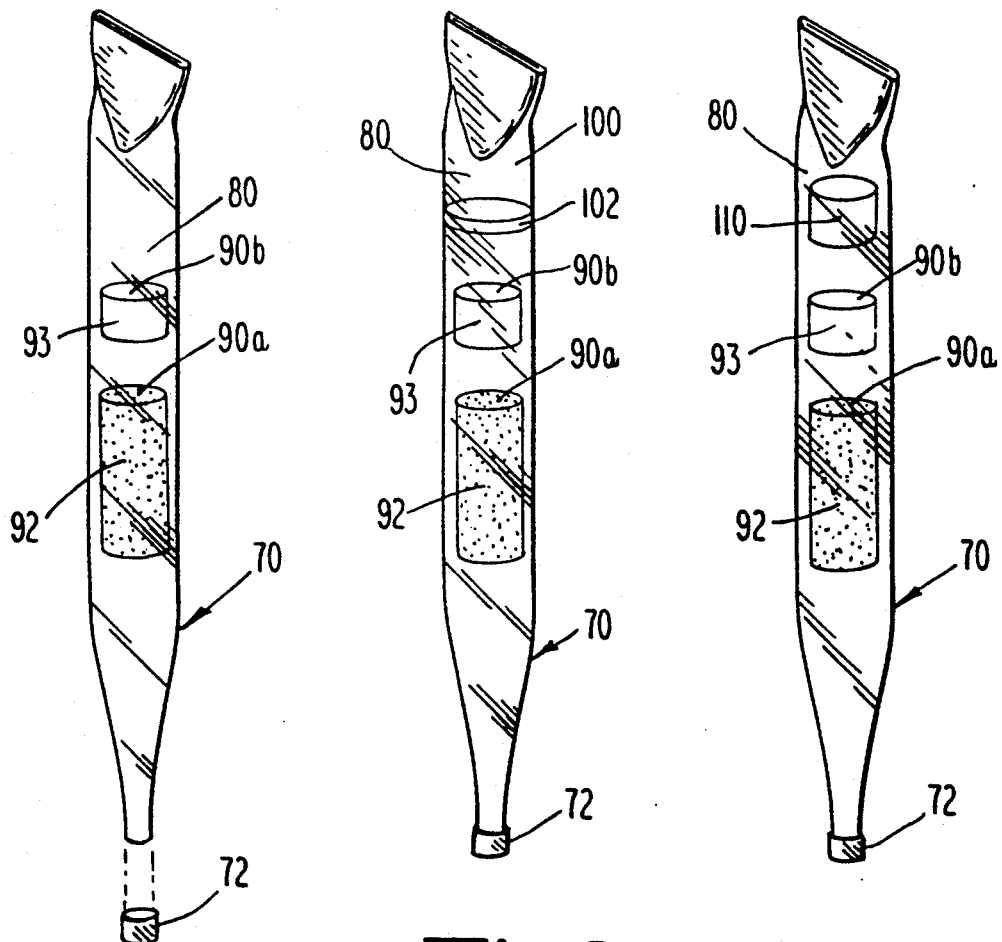

LATEX AGGLUTINATION ASSAY

FIELD OF THE INVENTION

This invention relates to methods and products for detecting the presence of specific chemical compounds in a variety of materials. More particularly, this invention relates to methods and products for the detection of biologically important ligands such as drugs, drug metabolites, and other haptens by an accurate assay technique which is faster, simpler, and less expensive than those previously known in the art.

BACKGROUND OF THE INVENTION

A great deal of research has been directed to the development of accurate techniques for determining the presence of organic materials such as drugs, drug metabolites, contaminants, pollutants, and the like in substances of interest such as food, soil, and bodily fluids. For example, pathological or other conditions in human beings and animals are often detected by performing immunoassays on samples of bodily fluids such as urine or blood serum. Immunoassays are based on the capacity of a first compound, known as a ligand, to recognize or bind a second compound, known as a receptor, having a specific spatial and/or polar organization. Typically, immunoassays are used for the detection of antibodies, antigens, or haptens in bodily fluids.

Antigens are foreign substances which, when introduced into a higher animal, bring about the formation of antibodies which react with the antigens to initiate protection against infection or disease. A single antigen may contain multiple antigenic determinants, also known as active sites, which are regions of the antigen molecule that specifically elicit the production of antibody to which the antigenic determinant binds.

Antigens are to be contrasted with haptens, which are relatively small molecules that cannot alone elicit the production of antibodies. A hapten can act as an antigenic determinant and elicit antibody synthesis only when covalently attached to a larger carrier molecule. However, when detached from its carrier, the hapten will retain its ability to bind strongly to the antibody, albeit via what is believed to be a single active site.

The presence of an antigen, hapten, or antibody in a sample of bodily fluid typically can be confirmed or determined by contacting the corresponding antibody or the corresponding antigen with the sample. The presence or absence of the antigen, hapten, or antibody in the sample is usually established by detecting the occurrence or nonoccurrence of a reaction between the specific ligand/receptor pair. For example, the reaction between an antibody and an antigen usually manifests itself by insolubility or agglutination.

Because most ligand/receptor pairs are detected only with difficulty, it is frequently necessary to use certain inert carrier moieties to facilitate their detection. For example, in certain latex agglutination techniques an antibody and/or an antigen is covalently bound to discrete latex particles having diameters on the order of about 0.01 to about 100 micrometers. These particles are cross-linked or otherwise aggregated by the complementary antigen or antibody by way of the multiple binding sites found on both moieties. The agglutination of such particles into relatively large aggregates or clumps is then observed.

A slightly different situation is presented in detecting a hapten by latex agglutination. Since haptens possess but a single active site, haptens and their complementary antibodies do not "cross-link" or form long aggregates. Thus, it is necessary in latex agglutination techniques for the detection of haptens that the hapten be bound to the latex particles. The hapten present in a sample typically is then detected by its capacity to inhibit the agglutination of antibody-bearing particles and hapten-bearing particles. In such systems, a negative test for hapten is manifested by agglutination of antibody- and hapten-bearing particles and a positive test is manifested by the absence of such agglutination.

One serious problem with hapten detection by such techniques is that hapten-bearing particles are somewhat unstable and will often agglutinate with one another to form multiple-particle aggregates. Thus, it is known in the art to stabilize mixtures containing hapten-bearing latex particles with stabilizing factors, such as bovine serum albumin. However, these stabilizing factors are sometimes diluted by urine or serum during the course of a latex immunoassay, leading to agglutination of the hapten-bearing particles, even in the absence of antibody-bearing particles. Agglutination in this manner makes it difficult or impossible to effectively determine the presence of hapten in many types of samples.

The different types of latex agglutination techniques presently known in the art may be categorized into three basic classes based upon the particular method employed for detecting ligand/particle aggregates. The techniques of the first class involve centrifugation. For example, U.S. Pat. No. 4,738,932 in the name of Yabusaki discloses a centrifugation technique which involves rotating an agglutination slide on a serological rotator and then using a magnifier to examine slide wells for agglutination.

The second class comprises techniques which detect aggregates by particle counting. For example, Masson, et al., *Methods in Enzymology*, 1981, 74, 106–139, disclose an immunoassay technique in which a complicated device which uses forward light scattering is employed to count unaggregated particles. Thus, both the centrifugation and particle counting techniques have the disadvantages of complicated, time-consuming procedures and expensive, highly specialized devices.

The techniques of the third class are those in which agglutination is detected visually. However, since the average human eye can only detect particles down to about 40 micrometers in diameter, most visual agglutination tests must produce relatively large aggregates which typically require an undesirably long time to form. U.S. Pat. No. 4,459,361, in the name of Gefter, discloses a somewhat improved type of visual technique which involves visual detection of unaggregated particles rather than aggregated particles. In certain techniques according to Gefter, both the ligand and the receptor are separately immobilized on latex particles and then mixed with a sample of bodily fluid suspected to contain the ligand. In other techniques, the sample is incubated with the receptor and with latex particles bearing the ligand. According to Gefter, the ligand in the sample competes with the ligand-bearing particles for the receptor sites. To the extent that the ligand contained in the sample binds to the free receptor or receptor-bearing particles, the ligand-bearing particles fail to aggregate. Thus, when such a mixture is exposed to a filter having a controlled pore size there is a substantial increase in the amount of unaggregated, ligand-bearing particles which pass through the filter. It is the presence of these unaggregated particles which is then detected.

According to Gefter, the amount of unaggregated particles which pass through the filter is proportional to the amount of ligand in the sample. Further, Gefter states that the number of unaggregated particles is sufficient to be visible to the naked eye, and that this visibility can be enhanced by the selection of the size, color, optical density, or fluorescence of the particles.

However, the techniques disclosed by Gefter have a number of serious shortcomings. For example, certain techniques require that both ligand- and receptor-bearing particles be prepared, thus adding considerable time and expense. While Gefter asserts that the unaggregated, ligand-bearing particles can be detected with the naked eye, the provided examples do not detect such particles visually, but rather with sophisticated spectrophotometric devices. Moreover, the teachings of Gefter do not appear applicable where the ligand is a hapten. To the extent that hapten contained in a sample binds to antibody, hapten-bearing particles would be expected to aggregate and effect a decrease, rather than an increase, in the amount of unaggregated, hapten-bearing particles which pass through the filter.

Accordingly there still exists a need for relatively simple, inexpensive techniques for the accurate detection of biologically important chemical compounds such as drugs, drug metabolites, and other haptens which may be present in bodily fluids.

OBJECTS OF THE INVENTION

It is therefore one object of the present invention to provide methods and products for detecting the presence of chemical compounds in a variety of substances.

It is another object of this invention to provide methods and products for accurately detecting biologically important ligands, particularly drugs, drug metabolites, and other haptens.

It is still another object of this invention to provide methods and products for detecting biologically important ligands which are faster, simpler, and less expensive than those known in the art.

It is a further object of this invention to provide improved methods and products for performing latex agglutination immunoassays for drugs, drug metabolites, and other haptens.

SUMMARY OF THE INVENTION

These and other objects are achieved by the present invention, which provides methods and apparatus for determining the presence of a ligand such as a hapten in a sample suspected to contain the ligand. The methods and apparatus depend upon a color visualization indicating the ligand's presence or absence in the sample. This color visualization does not require the use of complicated instrumentation or equipment. All color changes are readily detected by the average naked human eye.

The preferred methods of this invention comprise providing a reagent system which comprises a plurality of particles which have the capacity to form multiple-particle aggregates and which bear on their surface a ligand which is the same as or different than the ligand suspected to be present in the sample. The reagent system further comprises an amount of receptor which is specific for both the ligand in the sample and the ligand borne on the particles. The amount of receptor is sufficient to stabilize the particles.

The methods further comprise forming a test mixture by contacting the reagent system with the sample and passing the test mixture through a filter having apertures which are larger than the particles but smaller than the aggregates, thereby producing a filtrate. The color of the filtrate is then analyzed for the presence of the ligand-bearing particles. The absence of ligand in the sample is confirmed by the presence of ligand-bearing particles in the filtrate, while presence of ligand in the sample is confirmed by the absence of ligand-bearing particles in the filtrate.

The present invention also provides reagent systems which comprise particles which bear a ligand on their surface and which have the capacity to form multiple-particle aggregates. The reagent systems further comprise a stabilizing amount of a receptor specific for the ligand. Preferred reagent systems comprise hapten-bearing particles and a stabilizing amount of an antibody specific for the hapten. The reagent systems are more stable than those known in the art, as the hapten-bearing particles will not aggregate with one another upon dilution with a sample unless the sample contains the hapten.

Also provided are assay plates and reaction cells suitable for performance of the methods disclosed. Preferred assay plates comprise a top member having a filter well and an observation well. The assay plates further comprise filter means adjacent the top member and extending across the filter well, wicking means adjacent the filter means and extending the length and width of the filter well and the observation well, and a bottom member adjacent the wicking means. In preferred embodiments, the top member, filter means, wicking means, and bottom member are held in position with an appropriately applied adhesive.

Reaction cells according to this invention comprise ligand-bearing particles and a stabilizing amount of a receptor specific for the ligand. Preferably, the reaction cell is a pipette which contains colored particles and the stabilizing amount of receptor in separate breakable vessels within the pipette. In certain other embodiments, the reaction cell further comprises a kill solution to inactivate all biologically active materials employed in performing the assay.

The methods generally can be performed more rapidly than other visually-detected immunoassays, as the relatively small aggregates which indicate the presence of ligand in the present invention form more rapidly than the larger particles required by prior art techniques. Also, the methods and apparatus are as sensitive as prior immunoassay techniques, but do not require complex, time-consuming manipulative steps nor expensive and complicated devices. Thus, the present methods and apparatus can conveniently be used by persons having little or no technical training.

BRIEF DESCRIPTION OF THE DRAWINGS

FIG. 4 is an exploded sectional view of an assay plate according to the present invention having beneath the filter well a substrate which comprises ligand-bearing particles and a stabilizing amount of a receptor specific for the ligand.

FIG. 5 is a perspective view of a reaction cell according to the present invention.

FIG. 6 is a perspective view of a reaction cell according to the present invention comprising kill solution in a compartment.

FIG. 7 is a perspective view of a reaction cell according to the present invention comprising kill solution in a breakable vessel.

DETAILED DESCRIPTION OF THE INVENTION

Figure 1:
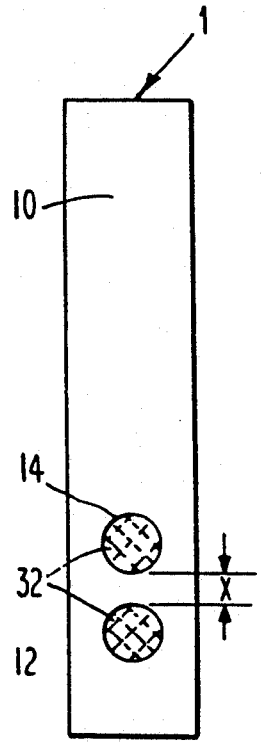
FIG. 1 is a top plan view of an assay plate according to the present invention.
Figure 2:
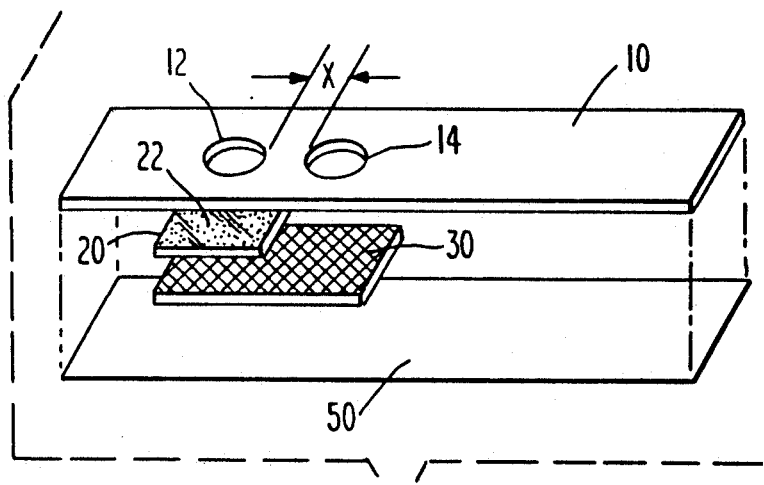
FIG. 2 is an exploded sectional view of an assay plate according to the present invention.

The present invention provides a sensitive and accurate yet simple method for determining relatively low concentrations of a wide variety of ligands which may be present in various, sampled substances. The invention can be applied to detect a wide variety of ligands contained in samples of bodily fluids, such as urine, serum, and plasma, derived from mammals, especially humans. The present invention also provides reagent systems which may be employed in certain of the disclosed methods.

It will be appreciated that the term "ligand" denotes all constituents in bodily fluids, cell extracts, and tissue extracts for which there is present or can be formed an immunological reaction partner. Antigens, haptens, and antibodies are ligands according to this invention, as are amides, amino acids, peptides, proteins, lipoproteins, glycoproteins, sterols, steroids, lipoids, nucleic acids, enzymes, hormones, vitamins, polysaccharides, and alkaloids. Preferred ligands are those having a single active site. Those skilled in the art will appreciate that the active site of a ligand is that portion that binds a receptor for the ligand. A preferred type of ligand having a single active site is a hapten.

Representative examples of antigens and haptens are the "materials" set forth in U.S. Pat. No. 4,256,834 in the names of Zuk, et al., which is incorporated herein by reference. Preferred antigens include the proteins derived from cultures of HIV-1 virus, cytomegalovirus, HIV-2 virus, hepatitis-B virus, hepatitis-C virus, herpes 1 and 2 virus, HTLV-1 virus, chlamydia virus, *Borrelia burgdorferi, Treponema pallidum, Neisseria gonorrhoeae,* staphylococcus, and the streptococci of groups A and B.

It will be appreciated that while haptens are not antigens per se, they are capable of functioning as antigens when coupled with a suitable carrier molecule. Drugs and drug metabolites provide excellent examples of haptens, the term "drug" encompassing any substance, other than a food, used in the prevention, diagnosis, alleviation, treatment, or cure of disease in man and animals. Substances prescribed by a registered physician are included within the term "drug", as are self-prescribed substances whose use is prohibited by law. Preferred haptens include tetrahydrocannabinol and its metabolites, cocaine and its metabolites, morphine and other opiates, amphetamine, phencyclidine, barbiturates, steroids, human chorionic gonadotropin, luteinizing hormone, and theophylline.

According to one aspect of the present invention, a sample suspected to contain a ligand of interest is contacted with a reagent system which comprises particles which have the capacity to form multiple-particle aggregates and which bear the ligand on their surface, along with a stabilizing amount of a receptor specific for the ligand. The receptor is present in an amount sufficient to stabilize the particles upon dilution by the sample. Where the ligand is a hapten and the receptor is an antibody to that hapten, it is believed that the antibody stabilizes the mixture by binding with the hapten which is bound to the particle in an orientation that presents the negatively charged carboxyl terminal end of the antibody away from the particle. These carboxyl groups repel adjacent particles and stabilize the particle mixture.

While it is preferred that the ligand borne on the particles be the same as the ligand suspected to be contained in the sample, the ligands need not be identical. Those skilled in the art will appreciate that non-identical ligands may share a community of properties, most notably a common active site, such that a single receptor may be specific for both ligands. Hence, it is possible in accordance with the present invention to employ particles which bear on their surface a ligand which is different from the ligand suspected to be contained in the sample, so long as the receptor employed is specific for the both ligands. For example, it is known that heterophil antigens can be used in the detection of antibodies induced during infectious mononucleosis.

Where the sample contacted with the reagent system does not contain a ligand of interest, no agglutination is observed. However, where the sample does contain a ligand such as a hapten, the antibody preferentially binds with this "free" hapten, not the hapten which is bound to the particles. Without the stabilizing effect of the antibody, the hapten-bearing particles agglutinate. Thus, where the ligand is a hapten, ligand-bearing particles have the capacity to form multiple-particle aggregates, particularly in the absence of a stabilizing amount of receptor.

The respective quantities of the receptor and the ligand-bearing particles contained in the reagent system are preferably selected such that there is a relatively high concentration of particle-bound ligand and a relatively low concentration of receptor. It is important that the receptor is substantially reacted with the ligand which is bound to the particles; that is, there should be no excess receptor. Also, the amount of receptor found in the reagent system should be selected such that essentially all the receptor reacts with the ligand which is contained in the sample upon contacting the reagent system and the sample.

The particles may be of any latices which are known or believed to be employable for latex agglutination, such as exemplified by the homopolymers and copolymers produced from styrene or its derivatives such as methylstyrene, ethylstyrene, and chlorostyrene, olefins such as ethylene and propylene, acrylic acid or its esters such as methyl acrylate and ethyl acrylate, methacrylic acid or its derivatives such as ethyl methacrylate, acrylonitrile, and acrylamide, dienes such as butadiene, chloroprene, and isoprene, vinyl chloride, vinylidine chloride, and vinyl acetate. The latices of homopolymers or copolymers made of polystyrene or styrene primary amines are preferred.

Other types of particles include carboxylated polystyrene, with or without reactive groups to facilitate reaction with the receptor, such as amino groups, thiol groups, carboxyl groups or other reactive groups. Butadiene/styrene copolymers such as carboxylated styrene butadiene or acrylonitrile butadiene styrene are also useful. Inorganic particles, such as silicas, clay, carbons such as activated charcoal, and other materials on which the ligand can be immobilized can be used in the present invention.

It is important that the particles are of approximately the same diameter, so that they will easily pass through the same size filter aperture. The particles should have mean diameters of about 0.01 to about 100 micrometers, preferably about 0.01 to about 10 micrometers. More preferably the mean diameter of the particles is about 0.3 micrometers and the diameters of the particles do not vary from the mean by more than 30%, preferably not by more than 15%.

The particles preferably have a visually recognizable color produced by the addition of dyes, pigments, or coatings. For example, the preparation of dyed polyacrylamide particles is disclosed in U.S. Pat. No. 4,108,974 in the names of Wegfahrt, et al., which is incorporated herein by reference. It is preferred that the color be relatively dark, preferably black or dark blue.

Preferred particles are the small, uniform diameter colored polystyrene or styrene primary amino latex spheres available in a variety of diameters from Bangs Laboratories of Carmel, Ind. or Seradyn, Inc. of Indianapolis, Ind.

The treatment of latex particles with the a second ligand corresponding to the first ligand suspected to be contained in the sample can be effected by any of the methods known in the art. The treatment conditions will understandably vary to some degree depending upon the physicochemical properties of the latex particles, the ligand, and the receptor. In accordance with preferred embodiments, a ligand is covalently bound to a particle of defined dimensions, preferably a latex particle having a spherical shape and defined, uniform diameter. The ligand can be an antigen, antibody, an enzyme, or any protein or other material which specifically binds to the receptor. It is preferred that the ligand be a hapten. While it is preferred that the ligand be chemically bonded to the latex particles, the particles may alternatively be coated with a substance to which the ligand will adhere, so long as the coating does not interfere with the binding between the ligand and the receptor. The relative amounts of immobilized ligand and particles are preferably adjusted so that the receptor will react with ligand contained in the sample and the ligand-bearing particles will aggregate with one another after when a sample containing a corresponding ligand is mixed with the reagent system for a reasonable interval.

The sample and reagent system may be contacted in a number of ways. In a preferred method, the sample is mixed with a solution which comprises the ligand-bearing particles, the stabilizing amount of receptor, and other reagents necessary to promote the agglutination reaction, forming a test mixture. An interval is permitted to pass which is sufficient for agglutination to occur or for multiple-particle aggregates to otherwise form. Alternatively, the sample can be passed through a substrate such as a glass membrane which contains the ligand-bearing particles, the stabilizing amount of receptor, and other reagents necessary to promote the agglutination reaction. Aggregates and other moieties may be released from the substrate. The released aggregates and other moieties also constitute test mixtures according to this invention.

The test mixture is then exposed to a filter having apertures which are larger than the particles but generally smaller than the clumps of multiple-particle aggregates which may have formed. The filter should have a defined pore size which is about 5 to about 15 times larger than the latex particle diameter, preferably about 10 to about 12 times larger, more preferably about 3 micrometers in diameter. It will be appreciated that there may be some small variance in the diameters of the pores. Preferably, the pore diameters will not vary from the nominal diameter by more than 30%, preferably not by more than 15%.

The pore size of the filter is chosen to retain multiple-particle aggregates yet permit the passage of the relatively small aggregates which may be formed by non-specific agglutination. It will be appreciated that non-specific agglutination is the aggregation of ligand-bearing particles in the absence of ligand in the sample. The sensitivity of the assay should be adjusted to produce aggregates larger than the pore size, roughly 10 to 15 particles in diameter. Preferably, the filter is an absolute channel membrane having pores of controlled diameter. Preferred controlled pore membranes comprise polycarbonate, such as those commercially available from the Poretics Corporation of Livermore, Calif.

Once the mixture is filtered, the filtrate produced thereby is analyzed for the presence of ligand-bearing particles which are unaggregated or non-specifically aggregated. While it will be appreciated that such analysis may be performed by any of the appropriate physical and/or chemical methods known in the art, such as centrifugation or particle counting, analysis of the filtrate is preferably performed by visually inspecting the filtrate to determine the presence therein of a recognizable color corresponding to the latex particles. Thus, where the proportions of ligand, receptor, and ligand-bearing particles have been carefully selected, a qualitative system is established wherein the presence in the filtrate of a color corresponding to the particles indicates the absence of ligand in the sample, and the absence of such color in the filtrate indicates the presence of ligand in the sample. It is, of course, also possible to determine the quantity of ligand present in a sample in accordance with the present invention. A suitable quantitative system may be established by comparing the filtrate with one or more visual standards corresponding to known concentrations of colored particles in the filtrate. Such visual standards will be prepared from samples having known concentrations of ligand.

The present invention also provides apparatus suitable for implementing the described methods for ligand assay. In general, such apparatus comprise filter means for filtering the mixture produced by contacting a sample suspected to contain a ligand with a reagent system, as well as analysis means for determining the presence of the particles in the filtrate which passes through the filter.

A preferred apparatus for performing the methods of the present invention is an assay plate (1), examples of which are shown in FIGS. 1 through 4. The assay plates of this invention generally comprise: a substantially flat top member (10) of predetermined dimensions having a filter well (12) and an observation well (14); filter means (20) adjacent the top member and extending across the filter well; wicking means (30) adjacent the filter means and extending the length and width of the filter well and the observation well; and a substantially flat bottom member (50) having the approximate dimensions of the top member, adjacent the wicking means. It will be appreciated that analysis means comprises elements of the assay plates other than the filter means.

The top member preferably comprises a material which is substantially impermeable to aqueous solutions such as associated with human body. The top member preferably is cut or stamped from a rigid material and, thus, is able to impart some degree of support to the assay plate. It is preferred that the top member comprise polystyrene and have a length of about 100 millimeters, a width of about 20 millimeters, and a thickness of about 1.0 millimeters.

The top member should be cut, stamped, or otherwise fabricated to have a filter well (12) and an observation well (14) extending though the entire thickness of the top member. Preferably, the filter well and the observation well are circular, but other shapes are possible. It is also preferred that the filter well and the observation well be a predetermined distance (X) from one another. Since there exists the possibility that some multiple-particle aggregates might not form clumps of sufficient diameter to be retained by the filter, the predetermined distance (X) is selected such that any aggregates which pass through the filter do not reach the observation window. Thus, the predetermined distance (X) may vary with the specific ligand, receptor, particle, and wicking means employed. While the predetermined distance (X) should be determined empirically, it will generally be the case that the distance varies in an inverse fashion with the capacity of the wicking means to retain aggregates.

The filter means (20) is preferably a filter as described above having apertures (22) which are larger than the particles bu generally smaller than the clumps of multiple-particle aggregates. It is preferred that the filter means be a controlled pore polycarbonate membrane. While the filter means need only extend across the filter well, where the filter means is transparent or nearly transparent, such as where the filter means is a controlled pore polycarbonate membrane, the filter means preferably also extends across the observation well, as in FIG. 3.

Adjacent the filter means is the wicking means (30). The wicking means is preferably positioned in close physical contact with the filter means such that filtrate flows vertically into the wicking means and migrates horizontally from a position beneath the filter well to a position beneath the observation well. While the filter means need only extend the length of the filter well and the observation well, the wicking means is preferably somewhat longer, as in FIG. 3. The filter means and the wicking means are preferably attached to one another with a porous adhesive, such as the adhesive available from Adhesive Research Company of Glen Rock, Pa. under the tradename ARcare Porous. It is preferred that the wicking means comprise non-woven fibers of glass or natural or synthetic polymeric materials, preferably polyester. The composition and arrangement of the fibers in the wicking means are selected such that the aggregates and the particles migrate thereon at different rates. Preferably the particles migrate faster. It is also preferred that the wicking means have an embossed or otherwise formed visually recognizable pattern, such as a crosshatch pattern (32), to facilitate the visual detection of color at the observation well.

The bottom member (50) is adjacent the wicking means and preferably comprises a material which is substantially impermeable to aqueous solutions. The bottom member preferably is cut or stamped to have the approximate width and length of the top member. The top member and/or the bottom member should serve to support the assay plate. Thus, where the top member provides adequate support, the bottom member may comprise a relatively non-rigid material, such as a vinyl polymer. The bottom member is preferably physically attached to the other components of the assay plate with an adhesive. Since many suitable adhesives impair the wicking properties of the wicking means, preferred assay plates have a barrier (40) such as a thin polyethylene film at least as long as the wicking means and positioned between the wicking means and the adhesive-bearing bottom member.

The assay plates of this invention optionally also comprise a substrate (60), such as a glass membrane, which comprises the ligand-bearing particles, the stabilizing amount of receptor, and other reagents necessary to promote the agglutination reaction. Such a substrate is to be employed where the sample is to be applied directly into the filter well, rather than pre-mixed with a solution containing the ligand-bearing particles and the stabilizing amount of receptor. The substrate should be positioned between the top member and the filter means and should extend across the filter well, as shown in FIG. 4.

The present invention additionally provides reaction cells for use in contacting a sample and the reagent system. A preferred type of reaction cell (70) is depicted in FIG. 5. One element of reaction cells according to this invention is a container (80) in which the reagent system may be contacted with a sample suspected to contain a ligand. Such containers may have a variety of shapes. However, a preferably-shaped container is a pipette, such as shown in FIG. 5. It will be appreciated that containers having an open end preferably further comprise a cap (72) for containing the sample and the reagent system. Preferred containers are disposable and comprise any of the relatively inexpensive, substantially transparent synthetic polymers known in the art, such as polyethylene. Suitable transparent pipette-shaped containers are available from Franklin, Inc. of Franklin, N.J.

Within a preferred reaction cell are breakable vessels (90a & 90b) which contain the reagent system. In certain preferred embodiments, vessel (90a) contains a solution (92) which comprises ligand-bearing particles, while vessel (90b) contains a solution (93) which comprises a stabilizing amount of receptor. Alternatively, the reagent system may be contained in a single vessel. The breakable vessels may comprise glass or some synthetic polymer, so long as the material employed has sufficient structural integrity to contain the components of the reagent system until they are to be contacted with each other and with the sample, at which time the vessels are broken or ruptured by applied force. Where a reaction cell contains a breakable vessel, it is necessary that the container comprise a relatively supple material through which such rupturing force may be applied to the breakable vessel.

Preferred reaction cells further comprise a kill solution. It is intended that the term "kill solution" denote any solution having the capacity to biologically inactivate the moieties — such as ligands, receptors, or samples — employed in performing a ligand assay. Solutions comprising ethanol, formaldehyde, glutaraldehyde, iodophors, or oxidizing bleaches provide examples of kill solutions according to this invention. It is preferred that kill solutions comprise oxidizing bleaches such as sodium hypochlorite. The kill solution is preferably contained in a compartment (100) at one end of the container and separated therefrom by a rupturable membrane (102). Alternatively, the kill solution is contained in a breakable vessel (110) located within the container. The membrane or vessel comprises a material which has sufficient structural integrity to contain the kill solution securely until broken or ruptured by applied force. The kill solution is then released and contacted with any biologically active substances located in the container or on the assay plate, usually upon the completion of an assay.

The present invention also provides kits useful for ligand assay. Certain of these kits comprise a reagent system and a filter means such as described above. Other kits comprise an assay plate and a reaction cell.

Additional objects, advantages, and novel features of this invention will become apparent to those skilled in the art upon examination of the following examples thereof, which are not intended to be limiting, wherein parts and percents are by weight unless otherwise indicated.

EXAMPLE 1

Cocaine metabolite was coupled to dyed styrene primary amino particles having a mean diameter of about 0.3 micrometers in a 50 millimolar 2-(N-morpholino) ethanesulfonic acid (MES) (pH=5.5) containing 10 mg/ml water soluble carbodiimide and 2 mg/ml aminocaproic acid for about 2.0 hours at room temperature. The particles were then filtered and washed in 50 millimolar MES (pH =5.5).

Cocaine metabolite was then added to these particles in 50 millimolar MES (pH=5.5) containing 10 mg/ml water soluble carbodiimide for about 2.0 hours at room temperature. The particles were filtered, washed, and re-suspended in phosphate buffered gelatin (pH=6.6) containing 0.67% glycerol and 0.01 gentamicin sulfate.

EXAMPLE 2

A solution comprising a 1:5000 dilution of anti-cocaine metabolite antibody, a 1:10000 dilution of sheep anti-mouse antibody, 0.75% bovine serum albumin, 12.5% polyethylene glycol, 0.15% sodium chloride, and 0.01% gentamicin sulfate was prepared.

EXAMPLE 3

Figure 3:
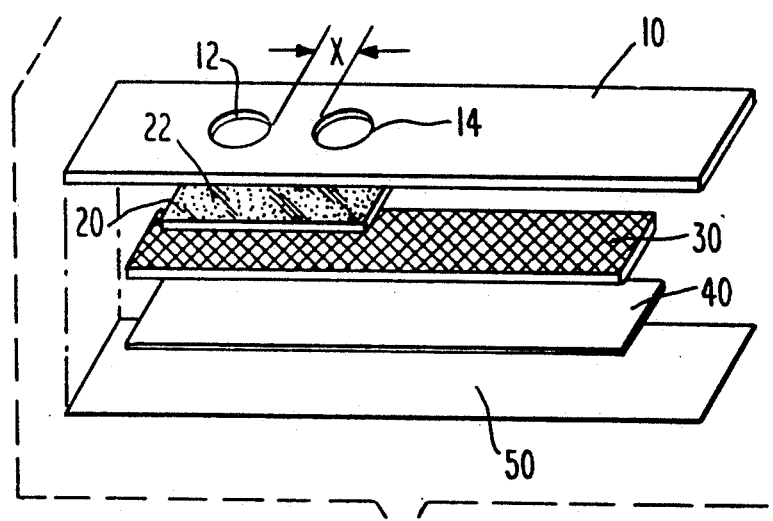
FIG. 3 is an exploded sectional view of a preferred assay plate according to the present invention having a barrier between the wicking means and the bottom member.

A 120 microliter sample of human urine known to contain cocaine metabolite was drawn into a pipette-shaped reaction cell such as shown in FIG. 5. One breakable vessel within the reaction cell contained 180 microliters of the solution prepared in Example 1. The second breakable vessel contained 240 microliters of the solution prepared in Example 2. The reaction cell was closed by replacing its cap and the breakable vessels were ruptured by squeezing it between the thumb and index finger. The reaction cell was then shaken gently. After about 60 seconds, the cap was removed and a few drops of the dark blue sample/receptor/particle mixture were placed in the filter well of an assay plate such as shown in FIG. 3. The assay plate had a polycarbonate membrane with controlled pores of about 3 micrometers and a polyester wicking layer. The distance (X) between the filter well and the observation well was 0.25 inches.

After about 1.0 minute, dark blue clumps of particle/ligand aggregates were observed in the filter well. No dark blue color was observed in the observation well.

It will be appreciated that had a reaction cell such as shown in FIG. 6 or FIG. 7 been employed instead of the reaction cell of FIG. 5, biologically active substances could next be inactivated by breaking or rupturing the membrane (102) or vessel (110) and contacting the released kill solution with the container and/or assay plate.

EXAMPLE 4

The procedure of Example 3 was repeated, except that a sample of urine known to not contain cocaine metabolite was used.

After about 1.0 minute, only a few clumps of particle/ligand aggregates were observed in the filter well. A dark blue color was observed in the wick material beneath the observation well.

EXAMPLE 5

A 120 microliter sample of human urine known to contain cocaine metabolite was pipetted into the filter well of an assay plate such as shown in FIG. 4. The assay plate had a glass membrane substrate (60) which had been saturated with the solution prepared in Example 1. The assay plate had a polycarbonate membrane with controlled pores of about 3 micrometers and a polyester wicking layer. The distance (X) between the filter well and the observation well was 0.25 inches.

After about 1.0 minute, dark blue clumps of particle/ligand aggregates were observed in the filter well. No dark blue color was observed in the observation well.

EXAMPLE 6

The procedure of Example 5 was followed, except that a sample of urine known to not contain cocaine metabolite was used.

After about 1.0 minute, no clumps of particle/ligand aggregates were observed in the filter well. A dark blue color was observed in the wick material beneath the observation well.

What is claimed is:

1. A method for determining the presence of a first ligand in a sample suspected to contain the first ligand, comprising:
    providing a reagent system which comprises:
        a plurality of particles which have the capacity to form multiple-particle aggregates and which bear on their surface a second ligand which is the same as or different than the first ligand; and
        an amount of a receptor which is specific for the first ligand and the second ligand, wherein the amount of receptor is sufficient to prevent formation of multiple-particle aggregates in the absence of the first ligand;
    forming a test mixture by contacting the reagent system with the sample;
    passing the test mixture through a filter having apertures which are larger than the particles but smaller than the aggregates, thereby producing a filtrate; and
    analyzing the filtrate to determine the presence of the particles, the presence of particles in the filtrate indicating the absence of the first ligand in the sample and the absence of particles in the filtrate indicating the presence of the first ligand in the sample.

2. The method of claim 1 wherein the first ligand and the second ligand each have one active site.

3. The method of claim 1 wherein the first ligand and the second ligand are each haptens.

4. The method of claim 1 wherein the receptor is an antibody to a hapten.

5. The method of claim 1 wherein the first ligand and the second ligand are each antigens.

6. The method of claim 1 wherein the receptor is an antibody to an antigen.

7. The method of claim 1 wherein the first ligand and the second ligand are independently selected from the group consisting of tetrahydrocannabinol and its metabolites, cocaine and its metabolites, morphine and other opiates, amphetamine, phencyclidine, barbiturates, steroids, human chorionic gonadotropin, luteinizing hormone, and theophylline.

8. The method of claim 1 wherein the sample comprises a mammalian bodily fluid.

9. The method of claim 1 wherein the particles have a mean diameter of from about 0.01 micrometers to about 10 micrometers.

10. The method of claim 1 wherein the particles have a mean diameter of about 0.3 micrometers.

11. The method of claim 1 wherein the particles comprise latex.

12. The method of claim 1 wherein the particles comprise polystyrene or styrene primary amino latex.

13. The method of claim 1 wherein the particles have a visually recognizable color.

14. The method of claim 1 wherein the contacting step is performed for a length of time sufficient to form multiple-particle aggregates.

15. The method of claim 1 wherein the contacting step is performed by contacting the sample with a solution which comprises particles and a solution which comprises the receptor.

16. The method of claim 1 wherein the contacting step is performed in a reaction cell.

17. The method of claim 1 wherein the contacting step is performed by contacting the sample with a substrate which comprises the reagent system.

18. The method of claim 1 wherein the filter comprises a controlled pore membrane.

19. The method of claim 1 wherein the filter comprises polycarbonate.

20. The method of claim 1 wherein the apertures are from about 5 to about 15 times larger than the particles.

21. The method of claim 1 wherein the apertures are from about 10 to about 12 times larger than the particles.

22. The method of claim 1 wherein the apertures are about 3 micrometers in diameter.

23. The method of claim 1 wherein the filtrate has a visually recognizable color.

24. The method of claim 1 wherein the analyzing step comprises visually determining the color of the filtrate.

25. The method of claim 1 wherein the analyzing step comprises comparing the appearance of the filtrate with a visual standard corresponding to a known concentration of the particles.

26. The method of claim 1 further comprising contacting the filtrate with a solution effective for inactivating biological moieties present in the filtrate.

* * * * *